United States Patent [19]

Willson et al.

[11] 4,020,829

[45] May 3, 1977

[54] SPRING GUIDE WIRE WITH TORQUE CONTROL FOR CATHETERIZATION OF BLOOD VESSELS AND METHOD OF USING SAME

[76] Inventors: James K. V. Willson; Marshall Eskridge, both of P.O. Box 2144, Mobile, Ala. 36601

[22] Filed: Oct. 23, 1975

[21] Appl. No.: 625,073

[52] U.S. Cl. .............................. 128/2 M; 128/2 A; 128/2.05 R; 128/348; 128/DIG. 9
[51] Int. Cl.² ................. A61B 10/00; A61M 25/00
[58] Field of Search ..... 128/2 B, 2 M, 2 A, 2.05 R, 128/348–351, DIG. 9

[56] References Cited
UNITED STATES PATENTS

| | | | |
|---|---|---|---|
| 3,452,742 | 7/1969 | Muller | 128/2 M |
| 3,500,820 | 3/1970 | Almen | 128/2 M |
| 3,547,103 | 12/1970 | Cook | 128/2.05 R |
| 3,749,085 | 7/1973 | Willson et al. | 128/2 B |
| 3,941,119 | 3/1976 | Corrales | 128/2 M |

FOREIGN PATENTS OR APPLICATIONS

| | | | |
|---|---|---|---|
| 156,901 | 12/1956 | Sweden | 128/348 |

*Primary Examiner*—Dalton L. Truluck
*Attorney, Agent, or Firm*—George H. Mitchell, Jr.

[57] ABSTRACT

An instrument for use in catheterization of small distal branch arteries includes a guide wire having a short flexible distal section connected with a relatively long, multi-wire, axial and rotary torque transmitting section to guide a soft, thin-walled, flexible catheter through the compound curves involved in the junctions between various arterial branches. A method for catheterization of blood vessels includes the steps of sequentially advancing the catheter and guide wire to negotiate these compound turns in the arterial system.

15 Claims, 10 Drawing Figures

SPRING GUIDE WIRE WITH TORQUE CONTROL FOR CATHETERIZATION OF BLOOD VESSELS AND METHOD OF USING SAME

This invention relates to an instrument for use in the catheterization of blood vessels for angiography (injection of contrast agents) for chemotherapy (control of bleeding) or other purposes. Many times, it is necessary to catheterize the smaller, more distal branch arteries and this often requires negotiating compound curves through several branchings.

One of the techniques used prior to the present invention utilizes a single strand guide wire, but this system suffers from the fact that it is practically impossible to control the transmission of rotary torque from the end of the wire which is being manipulated to the distal end being advanced through the arterial system.

Another prior technique involves the use of a flexible catheter within the walls of which braided wires are embedded. While this type of catheter is capable of transmitting rotary torque from one end to the other, it's disadvantages lie in the fact that the catheter is relatively stiff and, due to the embedded wires, it has a smaller caliber lumen relative to its external diameter. The increased stiffness of this braided wire catheter, as compared to a thinner-walled, flexible catheter made entirely of plastic, means that it can more easily damage the arterial wall and cannot negotiate many of the tight turns and curves. Also, the thicker wall of the wire embedded catheter also means that a larger hole is required in the entering artery for the same size lumen.

Therefore, it is an object of the present invention, to provide a guide wire which can be used with a thin-walled, flexible plastic catheter in which the distal portion of the guide wire is of a relatively short length and connected with a relatively long, manipulative section capable of transmitting rotational torque along its length whereby the rotation of the distal portion can be acurately controlled from the other end of the guide wire.

In a preferred form of the invention, the distal portion is normally curved. Various radii of curvature may be employed and the flexibility of the distal portion can vary in accordance with the type of use proposed. In practice, the torque control guide wire is moved axially through the catheter to advance the distal portion ahead of the catheter. In this position, the distal portion may be rotated by the manipulative section to engage the distal portion with the desired branch which is to be entered, after which the soft catheter is advanced over the guide wire. As each succeeding branch is reached, the procedure is repeated.

In another form of the invention, the flexible distal portion may be normally straight while the forward end of the catheter is formed with a normal curvature. In this modification, the guide wire is advanced to the point where the distal portion is placed at the forward end of the catheter and the entire assembly is rotated and advanced into the branch passageway. In this form of the invention, the purpose of the guide wire is to provide a reinforcement for the thin wall of the catheter, without which reinforcement, the catheter alone might simply wrinkle, or fold backwardly.

While the invention is intended primarily for the catheterization of blood vessels, it can be used in other areas of the body for catheterizing other organs such as veins, bronchial tree and intestinal tract (including the common bioduct).

Other objects and advantages will be apparent to those skilled in the art reading the following specification in connection with the annexed drawings, in which.

Figure 1:
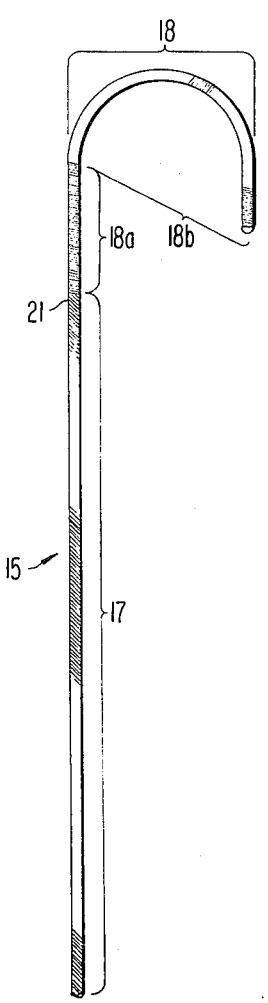
FIG. 1 is a plan view of a preferred form of guide wire in accordance with the present invention.

In the drawings, there is shown a guide wire, indicated generally by numeral 15, which is axially slidable within a soft, thin-walled, flexible catheter, indicated generally by numeral 16. As can be seen in FIG. 1, the guide wire comprises a relatively long, rotational torque transmitting section 17 which terminates in a normally curved distal portion 18, the latter having flexibility in bending as its primary characteristic and relatively little ability to transmit rotational torque.

Figure 5:
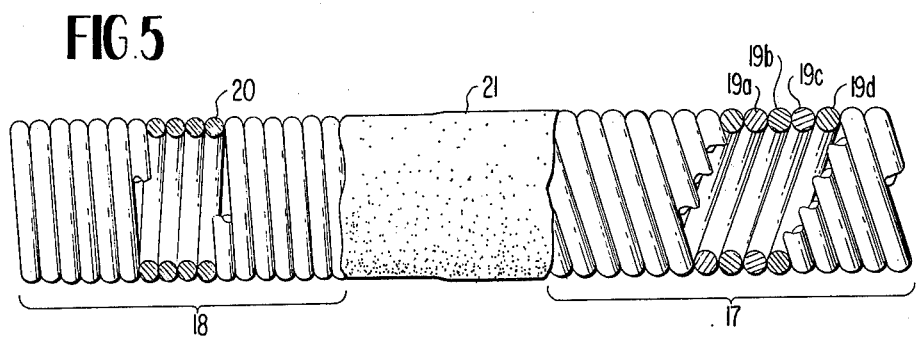
FIG. 5 is a fragmentary view on a greatly enlarged scale of a detail of construction of the guide wire.

As can be seen in FIG. 5, the relatively long, manipulative section 17 of the guide wire consists of a plurality (in this case four) of spring steel wires 19a, 19b, 19c and 19d wound closely together in a single layer helix having a uniform diameter along its length, the close spacing of adjacent turns of the wire making it possible to transmit force in an axial direction in compression. In addition, because there are a multiple number of parallel wires running the length of the entire section, the capability of this section for transmitting substantially large values of rotational torque from one each of the section to the other end is substantially increased over that of a single wire. A rotational torque transmitting wire helix of this type is disclosed and claimed in out prior U.S. Pat. No. 3,749,085, granted July 31, 1973.

The distal section 18 consists of only a single wire 20 wound in a single layer helix, with the adjacent turns closely abutting each other along the straight portion of the helix. The inner end of the distal section 18 can be joined in axial alignment to the outer end of the section 18 by means of soldering, indicated by numeral 20, or by any other suitable means and, conceivably, the section 18 might consist of an extension of one of the wires forming the helix 17. While the helix 18 is shown as having a diameter approximately the same as the helix 17, the diameter may vary and, in certain applications, might have a slight taper along its length. In the form of guide wire shown in FIG. 1, at least a portion of the distal portion of the helix 18 is normally formed to have a curvature, indicated by numeral 18b, which may vary according to the application in which the instrument is used. As is the case with the helix 17, the wire of helix 18 is closely spaced so that it is capable of transmitting compressional force in an axial direction so that there is substantially no lag in the forward movement of the distal portion 18b when axial advancing movement is imparted at the far end of helix 17. On the other hand, the single wire helix 18, while it is much more flexible than the multiple wire helix 17, the single wire, because of its "springiness" is relatively poor with respect to transmitting rotational torque with any degree of acurate control.

Figure 3:
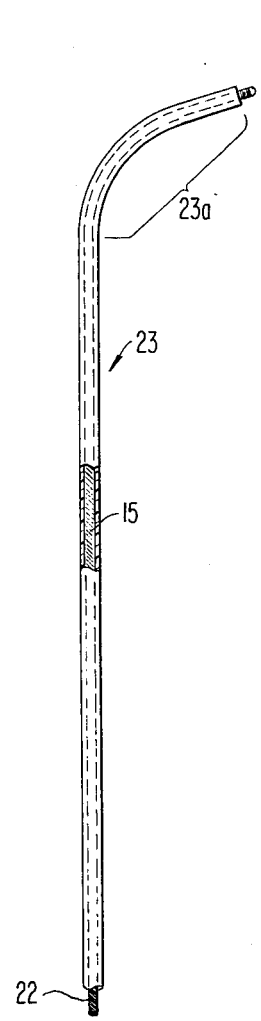
FIG. 3 is a plan view of the guide wire inserted within a catheter.

In FIG. 3, the guide wire 15 is shown as being fully inserted into a flexible catheter 23a, with the far end 22 of the helix 17 projecting downwardly from the lower end of the catheter. Assuming that the catheter is normally straight, the curved portion 18b of the guide wire will impart a curvature along a corresponding length 23a of the catheter.

Figure 2:
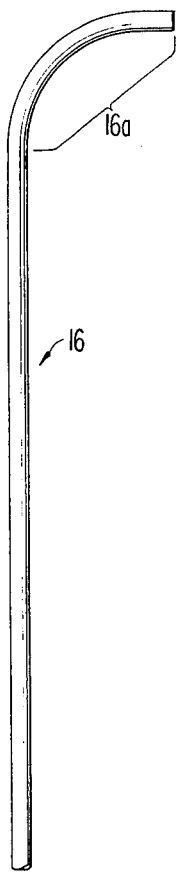
FIG. 2 is a plan view of a thin-walled, flexible, plastic catheter having its forward end provided with a normal curvature.
Figure 4:
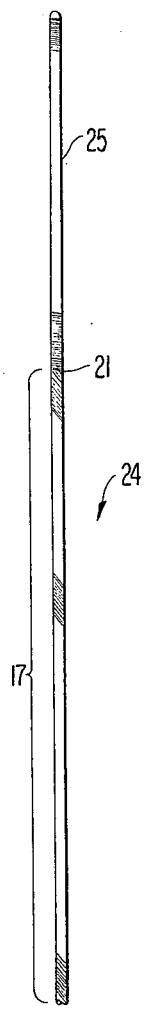
FIG. 4 is a plan view of a guide wire in which the flexible, distal portion is normally straight.

Under certain conditions, the curved guide wire 15 can be used with a curved catheter 16, in which case, the curvature imparted to the section 16a of the catheter will depend upon whether the rotary position of the guide wire is such that the curved portion 18b opposes or reinforces the curvature of the catheter. However, the curved catheter 16 of FIG. 2 is preferably used with the guide wire shown in FIG. 4 and indicated generally by numeral 24. This guide wire is similar to the previously described guide wire 15, in that it has a multi-wire rotational torque transmitting portion 17 of relatively great length joined at its upper end at 21 to a single wire helix 25 of relatively short length and great flexibility, forming a straight extension in alignment with the multi-wire section 17.

As a typical example of the technique of using the improved instruments described above, a description of the procedure to be followed in a femoral-cerebral angiography will now be described.

Entry into the arterial stream is made by a hollow needle puncture through the skin in the groin into the femoral artery. The distal portion, such as the portion 18 of the guide wire 15, is advanced into the artery through the needle and the needle is removed. This leaves the guide wire with its distal end 18 extending into the arterial lumen with its manipulative portion 17 extending outside the skin where it can be manipulated in axial and rotational directions either by means of the fingers or with the assistance of a conventional pin vise (now shown).

Figure 6:
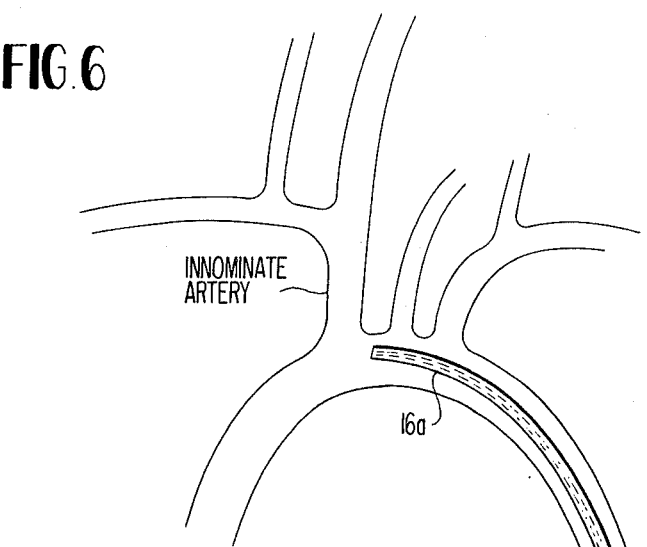
FIGS. 6–10 are schematic views of a typical arterial system showing successive steps in the use of the invention.
Figure 7:
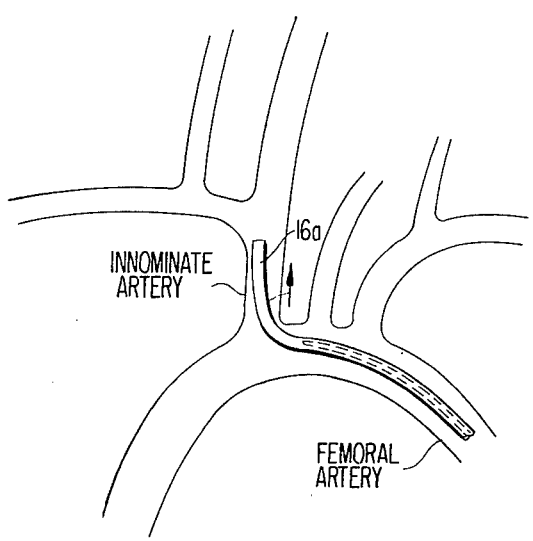
Figure 8:
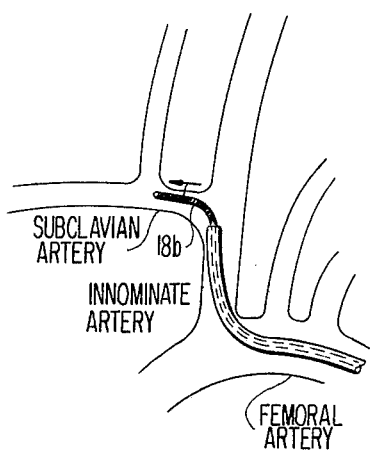
Figure 9:
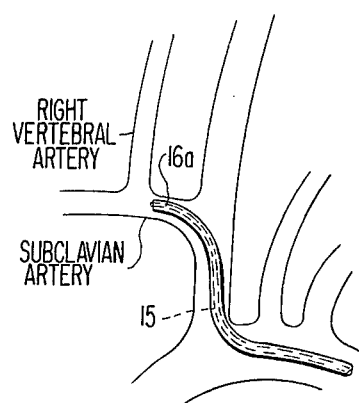
Figure 10:
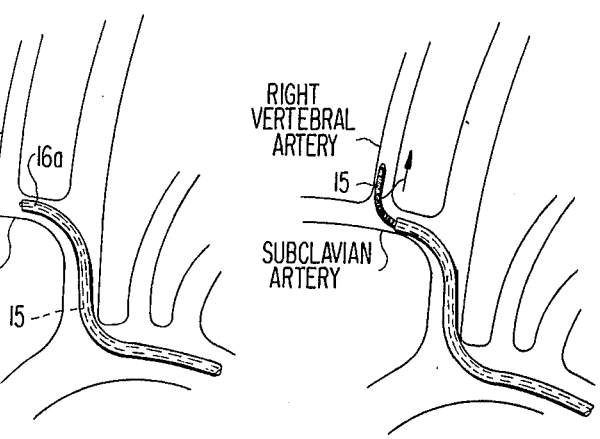

The next step is to introduce a catheter with a curved tip, such as the catheter 16 shown in FIG. 2, by pushing it over the projecting end 17 of the guide wire, into the femoral artery through the skin and up the femoral artery and up the aorta to the innominate artery to the position shown in FIG. 6. At this point, by manually rotating the catheter and advancing it further, the distal portion 16a can be maneuvered to enter the innominate artery without the assistance of the guide wire, as seen in FIG. 7. However, the soft flexible tip of the catheter will not be stiff enough to make the second turn into the subclavian artery because it lies in the opposite direction. This second turn into the subclavian artery is made by suitably advancing and rotating the guide wire to advance the distal portion 18b ahead of the catheter, as shown in FIG. 8. Following the advance of the guide wire, the catheter is also pushed forward and guided into the subclavian artery over the previously positioned guide wire, as shown in FIG. 9. To make the third turn into the right vertebral artery, the guide wire is again advanced and rotated into the branch artery as shown in FIG. 10 and, once it has entered, the catheter can be advanced as before.

The final step is to remove the guide wire entirely, leaving the catheter in place, ready for injection of fluid, with the tip of the catheter disposed in the vertabral artery and the other end extending out through the skin in the groin.

Instead of using the curved catheter of FIG. 2, a straight, flexible catheter can be used, in which case, all of the turns, including the first turn into the innominate artery, must be made by first advancing the curved tip of the guide wire into the branch artery, after which the straight catheter is advanced over the guide wire until it reaches the next turning point. However, when using the guide wire of FIG. 4, having a flexible distal portion 25, it is essential to use the curved catheter of FIG. 2. The difference in procedure is that, in this case, the guide wire is used primarily to reinforce the soft flexible catheter and when making a turn, such as the second and third turns in the example above, which might cause the catheter to buckle, the straight guide wire 24 is not advanced beyond the tip of the catheter but is pushed along with the curved catheter as it is rotated and advanced into successive branched arteries.

The advantages of the present invention can best be appreciated by a comparison between the dimensions of the thin-walled catheter which can be used with the procedure and guide wire of this invention, as compared with the dimensions of the wire-embedded catheters previously used. The inside diameter of a typical catheter according to this invention may be 0.055 inches; the outside diameter being 0.075 inches. This is to be compared with an inside diameter of 0.040 inches in the case of a wire-embedded catheter having an outside diameter of 0.090 inches. When it is considered that the flow of liquid through the catheter is a function of the area of the lumen which, in turn, varies as the square of the diameter, it will be realized that an increase of 189 percent in the area of the lumen can be obtained with the catheter of this invention, despite the fact that there is a reduction in the outside diameter of approximately 16 ⅔ percent. In the example of a catheter just described, the outside diameter of the helix would be approximately 0.038 inches. These figures are only exemplary and can be varied in accordance with the conditions and circumstances under which the instruments are to be used. Also, as stated previously, the technique described above in connection with the arterial system, can also be used in the catheterization of other organs such as the veins, bronchial tree and intestinal tract.

We claim:

1. Method for introducing fluid into a remote internal body passageway from a first internal organ from which said passageway is successively angularly branched utilizing two separate elongated elements, one of said two elements being a flexible, wholly non-metallic, hollow catheter, the other of said two elements comprising a flexible guide wire means having a helically wound single layer multi-wire coil capable of transmitting rotational torque at a one-to-one ratio along a first major portion of its length, the distal portion comprising a single wire helical coil having primarily flexibility in bending and capable of transmitting torque only in an axial compressional direction, the distal portion of one of said two elements having a normal curvature imparted to it during fabrication, comprising the steps of:

a. introducing the distal portions of said two elements in concentric relationship into said first internal organ;

b. advancing the distal portion of said element having a normal curvature into the entrance of a first branched passageway by axially manipulating a remote portion of said element having normal curvature from the exterior of the body;

c. rotating the distal portion of said element having normal curvature for entrance into said first branched passageway by rotatably manipulating said element having normal curvature from the exterior of the body;

d. advancing the distal portion of said catheter into said first branched passageway;

e. rotating the distal portion of the guide wire for entrance into a second passageway branching from the first passageway by rotation of the portion exterior of the body;

f. advancing the distal portion of the guide wire into said second passageway;

g. advancing said catheter into said second passageway;

h. removing said wire coil means;

i. introducing said fluid into said catheter.

2. The method of claim 1, wherein the distal portion of the wire coil means is provided with a normal curvature, including the step of introducing the distal end of the wire coil means into the second branched passageway prior to the introduction of the catheter into said second passageway.

3. The method of claim 1, in which the distal portion of the wire coil means is straight and the distal portion of the non-metallic catheter is provided with a normal curvature.

4. The method of claim 3, which includes the step of advancing said two elements simultaneously into said branched passageway.

5. The method of claim 4, which includes the step of rotating both of said two elements simultaneously prior to advancing said elements into said branched passageway.

6. Apparatus for introducing fluid into a remote internal body passageway from a first internal organ from which said passageway is successively angularly branched, including two elongated flexible elements, each having a length sufficient to introduce a distal portion into said remote branched passageway with a remote portion remaining outside the body:

a. one of said two elements comprising a hollow, flexible, wholly non-metallic catheter;

b. the other of said two elements comprising helically wound wire coil means, the major portion of its length comprising a smooth single-layer multi-wire closely wound helical coil capable of transmitting rotational torque at a one-to-one ratio from one end to the other, the short distal portion comprising a single-layer single-wire closely wound helical coil which is flexible in bending but capable of transmitting force in compression in an axial direction c. said two elements, when concentrically disposed, being freely axially slidable with respect to each other;

d. the distal portion of one of said two elements having a normal curvature imparted thereto during fabrication.

7. The invention defined in claim 6, wherein said normal curvature (d) has been imparted to the distal portion of said catheter (a).

8. The invention defined in claim 7, wherein the distal portion of said wire coil means (b) forms a continuous normally straight extension of the major portion of the wire coil means.

9. The invention defined in claim 7, wherein said catheter (a) comprises polyethylene.

10. The invention defined in claim 6, wherein said normal curvature (b) has been imparted to the distal portion of said wire coil means (b).

11. The invention defined in claim 6, wherein said single layer helix is of uniform diameter and all of the wires of the major portion of the wire coil means are normally contiguous to the adjacent wires throughout the circumference of each respective turn.

12. The invention defined in claim 11, wherein the distal portion of the wire coil means (b) is normally curved and the adjacent turns of wire of said single wire helix are contiguous to each other normally along only a portion of each turn.

13. The invention defined in claim 11, wherein said catheter (a) comprises polyethylene.

14. A guide implement for use in catheterizing various organs of the body, including veins, bronchial tree, intestinal tract and similar medical procedures comprising:

a. an elongated first helix composed of a plurality of metal spring wires laid in parallel contiguous relationship to each other throughout their lengths, each turn of each wire being of the same uniform diameter and the exterior of the helix being smooth along its length;

b. and a second helix having a uniform diameter composed of a single metal spring wire, the cross-section of said single wire being uniform throughout its length, said second helix having a normal longitudinal curvature imparted to it during fabrication;

c. one end of the second helix being joined to the first helix in alignment thereto, whereby the radial direction of curvature of the second helix can be accurately controlled by rotation of the first helix from outside the body.

15. The invention defined in claim 14, wherein said first helix (a) comprises four wires of uniform diameter.

* * * * *